United States Patent [19]

Rother et al.

[11] Patent Number: 6,083,414
[45] Date of Patent: Jul. 4, 2000

[54] COMPOSITION OF A MIXTURE OF A PHENOLIC COMPOUND AND AN AZOLE OR MORPHOLINE COMPOUND TO PROTECT ANIMAL HIDES AND LEATHER AGAINST MICROBES

[75] Inventors: Heinz-Joachim Rother, Krefeld; Martin Kugler, Leichlingen; Hartmut Rehbein, Krefeld, all of Germany

[73] Assignee: Bayer Aktiengesellschaft, Leverkusen, Germany

[21] Appl. No.: 09/213,584

[22] Filed: Dec. 17, 1998

Related U.S. Application Data

[62] Division of application No. 08/952,413, filed as application No. PCT/EP96/01845, May 3, 1996, Pat. No. 5,888,415.

[30] Foreign Application Priority Data

May 16, 1995 [DE] Germany ............... 195 17 840

[51] Int. Cl.$^7$ ...................... C14C 9/00
[52] U.S. Cl. ............ 252/8.57; 8/94.1 R; 8/94.18; 106/15.05; 106/18.32; 106/18.35; 424/405
[58] Field of Search ............ 252/8.57; 106/15.05, 106/18.32, 18.35; 8/94.1 R, 94.18; 424/405

[56] References Cited

U.S. PATENT DOCUMENTS

| 2,904,392 | 9/1959 | Pomerantz et al. ............ 422/23 |
| 5,223,524 | 6/1993 | Valcke ........................ 514/383 |
| 5,374,378 | 12/1994 | Lorentzen et al. .............. 252/380 |
| 5,378,406 | 1/1995 | Nagaoka ....................... 524/94 |

FOREIGN PATENT DOCUMENTS

| 341954 | 11/1989 | European Pat. Off. . |
| 366071 | 5/1990 | European Pat. Off. . |
| 409500 | 1/1991 | European Pat. Off. . |

OTHER PUBLICATIONS

WPIDS Abstract No. 96–131177, abstract of Spanish Patent Application No. 2081262 (Feb. 1996).

*Primary Examiner*—Anthony Green
*Attorney, Agent, or Firm*—Norris, McLaughlin & Marcus, P.A.

[57] ABSTRACT

The present application relates to the use of combinations of active compounds composed of phenolic active compounds and azole compounds for the preservation of animal hides and leather.

4 Claims, No Drawings

COMPOSITION OF A MIXTURE OF A PHENOLIC COMPOUND AND AN AZOLE OR MORPHOLINE COMPOUND TO PROTECT ANIMAL HIDES AND LEATHER AGAINST MICROBES

This application is a division of U.S. Ser. No. 08/952,413, filed Nov. 13, 1997, now U.S. Pat. No. 5,888,415 which is a 371 of PCT/EP96/01845 filed May 3, 1996.

The present application relates to the use of active compound combinations of phenolic active compounds with azole compounds for the preservation of animal hides and leather.

It is known that phenol derivatives and mixtures or formulations thereof can be used as products for the protection of materials in leather production. However, it has emerged that these compounds, used alone or in combination, do not provide sufficient protection against infections with microbes when storing hides and leather for a prolonged time.

Surprisingly, it has now been found that benzimidazoles, imidazoles, triazoles and/or morpholine derivatives in combination with phenolic compounds allow outstanding, long-term protection of the animal skins and leather during production and storage.

The invention therefore relates to the use of a combination of at least one triazole and/or at least one benzimidazole and/or at least one imidazole and/or at least one morpholine derivative with at least one phenolic compound for the protection of animal hides and leather during production and storage.

Suitable phenolic active compounds are preferably phenol derivatives, such as tribromophenol, trichlorophenol, tetrachlorophenol, nitrophenol, 3-methyl-4-chlorophenol, 3,5-dimethyl-4-chlorophenol, phenoxyethanol, dichlorophene, o-phenylphenol, m-phenylphenol, p-phenylphenol, 2-benzyl-4-chlorophenol, 2,4-dichloro-3,5-dimethylphenol, 4-chlorothymol, chlorphen, triclosan, fentichlor and their ammonium, alkali metal and alkaline earth metal salts, and also their mixtures.

Suitable triazole compounds are preferably triazoles such as amitrole, azocyclotin, azaconazole, BAS 480F, bitertanol, cyproconazole, climbazole, difenoconazole, fenbuconazole, fen-chlorazole, fenethanil, fluquinconazole, flusilazole, flutriafol, hexaconazole, imiben-conazole, isazofos, myclobutanil, metconazole, epoxyconazole, paclobutrazole, penconazole, propiconazole, cis-1-(4-chlorophenyl)-2-(1-1,2,4-triazol-1-yl)-cyclo-heptanol, tebuconazole, 2-(1tert-butyl)-1-(2-chlorophenyl)-3-(1,2,4-triazol-1-yl)-propan-2ol, tetraconazole, triadimefon, triadimenol, triapenthenol, triflumizole, triticonazole, uniconazole and their metal salts and acid adducts, and also their mixtures.

Suitable imidazoles are preferably compounds such as imazalil, pefurazoate, prochloraz, triflumizole, bifonazole, canesten, fluotimazole, miconazole, econazole, isoconazole, sulconazole and their metal salts and adducts and also their mixtures.

Suitable benzimidazoles are preferably compounds such as methyl benzimidazolyl-carbamate (MBC), benomyl, fuberidazole and thiabendazole.

Suitable morpholine derivatives are preferably compounds such as tridemorph, aldimorph, fenpropimorph, amorolfine and dodemorph.

Combinations of 3,5-dimethyl-4-chlorophenol, 2-benzyl-4-chlorophenol, p-chloro-m-cresol (CMC) and/or o-phenylphenol (OPP) as phenolic components and azoles such as tebuconazole, propiconazole, azaconazole, cyproconazole, climbazole, hexaconazole, epoxyconazole and/or imazalil as further components are preferred.

Combinations of the abovementioned preferred phenols with benzimidazoles such as MBC, benomyl and/or aldimorph or tridemorph are furthermore preferred.

Combinations of CMC and/or OPP with tebuconazole and/or propiconazole are particularly preferred.

Also preferred combinations are combinations of OPP and/or CMC with MBC.

In particular, a mixture comprising CMC, OPP and tebuconazole is used.

The mixing ratios of the phenolic component to the other active compounds is generally 5 to 200, preferably 10 to 100, in particular 12 to 50, parts by weight to 1 part by weight.

The ratio of the phenolic compounds to each other can be varied within wide limits and is preferably 1:1 to 1:5 in the case of a mixture of OPP and CMC.

The abovementioned mixtures of the active compounds are generally employed in the form of formulations. The use concentration is preferably 0.1 to 1% of mixture of active compounds based on the hides or leather to be protected.

In the compositions resulting from the formulation, the mixture of active compounds preferably amounts to 10 to 50%. The compositions comprise 10 to 30% of alkali metal hydroxides and/or alkaline earth metal hydroxides, 1 to 20% of ionic and/or non-ionic emulsifiers, 5 to 30% of organic solvents such as, in particular, glycols, ketones, glycol ethers, alcohols such as ethanol, methanol, 1,2-propanediol, n-propanol or 2-propanol, and 0–0.5% of perfumes and odoriferous substances as further components. The remainder to 100% is water.

The mixtures of active compounds and the compositions which can be prepared therefrom are used according to the invention in the production of leather for protecting animal hides against infection with, and damage caused by, microorganisms. The fact that representatives of the species Aspergillus niger Aspergillus repens, Hormoconis resinae, Penicillium glaucum and Trichoderma viride, Penicillium species such as P. citrinum or P. glaucum, Paecilomyces variotii, Cladosporium species, and Mucor species, such as Mucor mucedo, Rhizopus species, such as Rhizopus oryzae and Rhizopus rouxii can be suppressed completely and long-term is of particular interest.

The examples which follow are intended to illustrate the invention and are not limited thereto.

EXAMPLE 1

Agar plates are inoculated with conidia of the species Aspergillus niger Aspergillus repens, Penicillium glaucum, Trichoderma viride and Hormoconis resinae. Pieces of wet chrome leather (wet blue) which have been treated with mixture I and mixture II are subsequently placed on the agar, and the samples are incubated for 28 days at 20 to 30° C. and a relative atmospheric humidity of 95%.

| Mixture I | Mixture II |
| --- | --- |
| 30 parts by weight of p-chloro-m-cresol | 23 parts by weight of p-chloro-m-cresol |
| 13 parts by weight of o-phenylphenol | 10 parts by weight of o-phenylphenol |
| | 2 parts by weight of tebuconazole |

In the case of the wet blues preserved with mixture I, mould had grown on the test bodies after an incubation time of only 10 days. In the case of mixture II, no infection is observed after an incubation time of 28 days.

What is claimed is:

1. A microbiocidal composition useful to provide long-term protection of animal hides and leather against microbes, said composition comprising a synergistic amount therefor of a mixture of active ingredients comprising:

A) a first active ingredient, which is a phenolic compound selected front the group consisting of 3,5-dimethyl-4-clorophenol, 2-benzyl-4-chlorophenol, p-chloro-m-cresol (CMC), o-phenylphenol (OPP), and mixtures thereof, or an alkali metal salt or alkaline earth metal salt of said phenolic compound; and B) a second active ingredient, which is an azole or morpholine compound selected from the group consisting of tebuconazole, propiconazole, azaconazole, cyproconazole, climbazole, hexaconzole, epoxyconazole, imazali, methyl benzimidazolyl-carbamnate (MBC), benomyl, aldimorph, tridemorph, and mixtures thereof, or a metal salt or acid adduct of said azole or morpholine compound;

wherein the weight ratio of A : B in said composition ranges from 5:1 to 200:1 parts by weight.

2. The composition of claim 1, wherein said composition is a mixture of p-chloro-m-cresol (CMC) and/or o-phenylphenol (OPP) with tebuconazole and/or propiconazole.

3. The composition of claim 1, wherein said composition is a mixture of p-chloro-m-cresol (CMC) and o-phenylphenol (OPP) with tebuconazole.

4. The composition of claim 1, wherein said composition is a mixture of p-chloro-m-cresol (CMC) and/or o-phenylphenol (OPP) with methyl benzimidazolyl-carbamate (MBC).

* * * * *

UNITED STATES PATENT AND TRADEMARK OFFICE
CERTIFICATE OF CORRECTION

PATENT NO. : 6,083,414
DATED : July 4, 2000
INVENTOR(S) : Rother et al.

It is certified that error appears in the above-identified patent and that said Letters Patent is hereby corrected as shown below:

<u>Column 3,</u>
Line 18, delete "imazali" and substitute -- imazalil --

Signed and Sealed this

Twenty-sixth Day of February, 2002

Attest:

JAMES E. ROGAN
Attesting Officer     Director of the United States Patent and Trademark Office